United States Patent [19]
Howard et al.

[11] Patent Number: 5,854,239
[45] Date of Patent: Dec. 29, 1998

[54] DIAZABICYCLIC NEUOKININ ANTAGONISTS

[75] Inventors: Harry R. Howard, Bristol; Kevin D. Shenk, Groton, both of Conn.

[73] Assignee: Pfizer Inc., New York, N.Y.

[21] Appl. No.: 669,283

[22] PCT Filed: Nov. 14, 1994

[86] PCT No.: PCT/IB94/00352

§ 371 Date: Jun. 20, 1996

§ 102(e) Date: Jun. 20, 1996

[87] PCT Pub. No.: WO95/18129

PCT Pub. Date: Jul. 6, 1995

Related U.S. Application Data

[63] Continuation of Ser. No. 175,034, Dec. 29, 1993, abandoned.

[51] Int. Cl.[6] ............... C07D 471/08; C07D 487/08; A61K 31/435; A61K 31/495
[52] U.S. Cl. ............ 514/221; 540/556; 540/567; 540/477; 544/282; 544/477; 546/121; 514/300
[58] Field of Search ............ 546/121; 540/581, 540/582, 556, 567, 477; 544/282; 514/221, 300

[56] References Cited

U.S. PATENT DOCUMENTS 3,494,923  2/1970  Gubitz et al. ............ 260/268

FOREIGN PATENT DOCUMENTS 41-13031  7/1966  Japan.
WO 92/15585  9/1992  WIPO.

OTHER PUBLICATIONS

Hirshfeld, A. and Taub, W. Bridged bicyclic compounds, Tetrahedron. vol. 28, pp. 1275–1287, 1972.

*Primary Examiner*—Mukund J. Shah
*Assistant Examiner*—Bruck Kifle
*Attorney, Agent, or Firm*—Peter C. Richardson; Paul H. Ginsburg; B. Timothy Creagan

[57] ABSTRACT

The present invention relates to diazabicyclic compounds and, specifically, to compounds of the formula

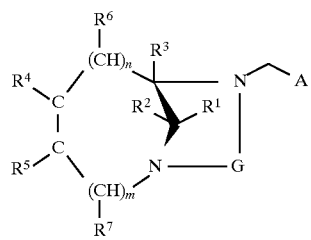

wherein A, G, $R^1$, $R^2$, $R^3$, $R^4$, $R^5$, $R^6$, and $R^7$ are as defined in the specification. The compounds of formula I are useful in the treatment of inflammatory and central nervous system disorders, as well as other disorders.

17 Claims, No Drawings

DIAZABICYCLIC NEUOKININ ANTAGONISTS

This application is a 371 of PCT/IB94/00352 filed Nov. 14, 1994 which is a continuation of Ser. No. 175,034 filed Dec. 29, 1993, now abandoned.

BACKGROUND OF THE INVENTION

The present invention relates to diazabicyclic compounds, pharmaceutical compositions comprising such compounds and the use of such compounds in the treatment and prevention of inflammatory and central nervous system disorders, as well as several other disorders. The pharmaceutically active compounds of this invention are substance P receptor antagonists.

Substance P is a naturally occurring undecapeptide belonging to the tachykinin family of peptides, the latter being named because of their prompt stimulatory action on smooth muscle tissue. More specifically, substance P is a pharmacologically active neuropeptide that is produced in mammals and possesses a characteristic amino acid sequence that is Illustrated by D. F. Veber et al. in U.S. Pat. No. 4,680,283. The wide involvement of substance P and other tachykinins in the pathophysiology of numerous diseases has been amply demonstrated in the art. For instance, substance P has been shown to be involved in the transmission of pain or migraine (see B. E. B. Sandberg et al., Journal of Medicinal Chemistry, 25, 1009 (1982)), as well as in central nervous system disorders such as anxiety and schizophrenia, in respiratory and inflammatory diseases such as asthma and rheumatoid arthritis, respectively, in rheumatic diseases such as fibrositis, and in gastrointestinal disorders and diseases of the GI tract such as ulcerative colitis and Crohn's disease, etc. (see D. Regoli in "Trends in Cluster Headache," edited by F. Sicuteri et al., Elsevier Scientific Publishers, Amsterdam, pp. 85–95 (1987)).

The following documents relate to compounds that exhibit activity as substance P receptor antagonists: U.S. Pat. No. 5,232,929; U.S. Pat. No. 5,138,060; WO 92/06079, published Apr. 16, 1992; WO 92/15585, published Sep. 17, 1992; WO 93/00330, published Jan. 7, 1993; WO 93/06099, published Apr. 1, 1993.

SUMMARY OF THE INVENTION

The present invention relates to compounds of the formula

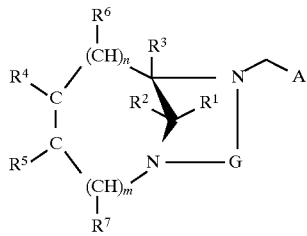

I or a pharmaceutically acceptable salt thereof wherein $R^1$ is phenyl, thienyl or benzhydryl wherein one of the phenyl moieties of said benzhydryl may optionally be replaced by naphthyl, thienyl, furyl or pyridyl and wherein said phenyl, thienyl and benzhydryl may be substituted with one or more substituents independently selected from halo, nitro, $(C_1-C_6)$alkyl optionally substituted with from one to three fluorine atoms, $(C_1-C_6)$alkoxy optionally substituted with from one to three fluorine atoms, amino, hydroxy$(C_1-C_6)$alkyl, $(C_1-C_6)$alkoxy$(C_1-C_6)$alkyl, $(C_1-C_6)$-alkylamino, $(C_1-C_6)$alkyl—O—CO—, $(C_1-C_6)$alkyl—CO—O—, $(C_1-C_6)$alkyl—CO—, $(C_1-C_6)$alkyl—O—, $(C_1-C_6)$alkyl—CO—$(C_1-C_6)$alkyl-, di-$(C_1-C_6)$alkylamino, —CONH—$(C_1-C_6)$alkyl, $(C_1-C_6)$-alkyl—CO—NH—$(C_1-C_6)$alkyl, —NHCOH and —NHCO—$(C_1-C_6)$ alkyl;

$R^2$ is hydrogen or $(C_1-C_6)$alkyl, or $R^1$ and $R^2$, together with the carbon to which they are attached, form a saturated carbocyclic ring having from 3 to 7 carbon atoms;

A is phenyl, thienyl, benzothiazolyl or naphthyl wherein said phenyl, thienyl, benzothiazolyl and naphthyl may be substituted with one or more substituents independently selected from halo, nitro, $(C_1-C_6)$alkyl optionally substituted with from one to three fluorine atoms, $(C_1-C_6)$alkoxy optionally substituted with from one to three fluorine atoms, amino, hydroxy$(C_1-C_6)$alkyl, $(C_1-C_6)$alkoxy$(C_1-C_6)$alkyl, $(C_1-C_6)$-alkylamino, $(C_1-C_6)$alkyl—O—CO—, $(C_1-C_6)$alkyl—CO—O—, $(C_1-C_6)$alkyl—CO—, $(C_1-C_6)$alkyl—O—, $(C_1-C_6)$alkyl—CO—$(C_1-C_6)$alkyl-, di-$(C_1-C_6)$alkylamino, —CONH—$(C_1-C_6)$alkyl, $(C_1-C_6)$-alkyl—CO—NH—$(C_1-C_6)$alkyl, —NHCOH and —NHCO—$(C_1-C_6)$alkyl;

n is 0, 1 or 2;

m is 0, 1 or 2;

the sum of n and m is 0, 1 or 2;

$R^3$ is hydrogen or $(C_1-C_6)$alkyl optionally substituted with one to three fluorine atoms;

$R^4$ and $R^5$ are hydrogen, or $R^4$ and $R^5$, together with the carbons to which they are attached, form an aromatic or non-aromatic carbocyclic or heterocyclic ring;

$R^6$ and $R^7$ are hydrogen, or $R^3$ together with $R^4$, $R^5$, $R^6$ or $R^7$, along with the carbon to which they are attached, form a saturated carbocyclic ring having from 3 to 6 carbons;

G is $(CR^8R^9)_p$ wherein p is an integer from 1 to 3, and $R^8$ and $R^9$ are each independently selected from hydrogen, $(C_1-C_6)$alkyl, phenyl, naphthyl and heteroaryl wherein said alkyl may be substituted by one to three fluorine atoms.

The term "heteroaryl", as used herein, unless otherwise indicated, includes thienyl, pyrrolyl, pyridyl, furanyl, quinolyl and indolyl.

The term "halo", as used herein, unless otherwise indicated, includes chloro, fluoro, bromo and iodo.

The term "alkyl", as used herein, unless otherwise indicated, includes saturated monovalent hydrocarbon radicals having straight, branched or cyclic moieties or combinations thereof.

The term "alkoxy", as used herein, includes O-alkyl groups wherein "alkyl" is defined as above.

The term "one or more substituents," as used herein, includes from one to the maximum number of substituents possible based on the number of available bonding sites.

Where reference is made in this application to "dialkylamino" substituents, the two alkyl groups in said dialkylamino are independently selected from $(C_1-C_6)$alkyl.

Preferred compounds of formula I include those wherein n is 0 or 1, m is 0 or 1 and p is 1 or 2.

Other preferred compounds of formula I are those wherein $R^1$ is phenyl or benzhydryl.

Other preferred compounds of formula I are those wherein A is 2-methoxyphenyl, 2-trifluoromethoxyphenyl or 5-methoxybenzothiazole.

Other preferred compounds of formula I are those wherein n is 1, m is 0, p is 1, $R^1$ is phenyl and A is benzothiazolyl.

Other preferred compounds of formula I are those wherein n is 0, m is 0, p is 1, $R^1$ is phenyl or benzhydryl and A is methoxyphenyl.

More preferred compounds of formula I are those wherein n is 1, m is 0, p is 1, $R^1$ is phenyl and A is methoxyphenyl, trifluoromethoxyphenyl or methoxy(trifluoromethoxy)phenyl.

More preferred compounds of formula I are those wherein n is 1, m is 0, p is 2, $R^1$ is phenyl and A is methoxyphenyl.

Specific preferred compounds of formula I include the following:

6-(2-methoxybenzyl)-8-phenyl-1,6-diazabicyclo[3.2.1] octane;

4-(2-methoxybenzyl)-9-phenyl-1,4-diazabicyclo[3.3.1] nonane.

Other preferred compounds of formula I include the following:

5-(2-methoxybenzyl)-10-phenyl-1,5-diazabicyclo[4.3.1] decane;

8-phenyl-6-(2-trifluoromethoxybenzyl)-1,6-diazabicyclo [3.2.1]octane;

6-(2-methoxybenzyl)-7-methyl-8-phenyl-1,6-diazabicyclo [3.2.1]octane;

6-(2-methoxybenzyl)-7,7-dimethyl-8-phenyl-1,6-diazabicyclo[3.2.1]octane;

7-benzhydryl-3-(2-methoxybenzyl)-1,3-diazabicyclo[2.2.1] heptane;

5-methoxy-6-(8-phenyl-1,6-diazabicyclo[3.2.1]oct-6-ylmethyl)benzothiazole;

5-methoxy-2-methyl-6-(8-phenyl-1,6-diazabicyclo[3.2.1] oct-6-ylmethyl)benzothiazole;

5-methoxy-2-phenyl-6-(8-phenyl-1,6-diazabicyclo[3.2.1] oct-6-ylmethyl)benzothiazole;

5-methoxy-2-trifluoromethyl-6-(8-phenyl-1,6-diazabiyclo [3.2.1]oct-6-ylmethyl)benzothiazole;

6-(2-methoxy-5-trifluoromethoxybenzyl)-8-phenyl-1,6-diazabicyclo[3.2.1]octane.

The present invention also relates to a pharmaceutical composition for treating or preventing a condition selected from the group consisting of inflammatory diseases (e.g., arthritis, psoriasis, asthma and inflammatory bowel disease), anxiety, depression or dysthymic disorders, urinary incontinence, gastrointestinal disorders such as emesis and colitis, psychosis, pain, sunburn, diseases caused by *Helicobacter pylori* or another urease-positive gram-negative bacterium, conditions that are caused or mediated by angiogenesis or of which angiogenesis is a symptom, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising an amount of a compound of the formula I, or a pharmaceutically acceptable salt thereof, effective in treating or preventing such condition, and a pharmaceutically acceptable carrier.

The present invention also relates to a method of treating or preventing a condition selected from the group consisting of inflammatory diseases (e.g., arthritis, psoriasis, asthma and inflammatory bowel disease), anxiety, depression or dysthymic disorders, urinary incontinence, gastrointestinal disorders such as emesis and colitis, psychosis, pain, sunburn, diseases caused by *Helicobacter pylori* or another urease-positive gram-negative bacterium, conditions that are caused or mediated by angiogenesis or of which angiogenesis is a symptom, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising administering to said mammal an amount of a compound of the formula I, or a pharmaceutically acceptable salt thereof, effective in treating or preventing such condition.

The present invention also relates to a pharmaceutical composition for antagonizing the effects of substance P in a mammal, including a human, comprising a substance P antagonizing amount of a compound of the formula I, or a pharmaceutically acceptable salt thereof, and a pharmaceutically acceptable carrier.

The present invention also relates to a method of antagonizing the effects of substance P in a mammal, including a human, comprising administering to said mammal a substance P antagonizing amount of a compound of the formula I, or a pharmaceutically acceptable salt thereof.

The present invention also relates to a pharmaceutical composition for treating or preventing a disorder in a mammal, including a human, resulting from an excess of substance P, comprising a substance P antagonizing amount of a compound of the formula I, or a pharmaceutically acceptable salt thereof, and a pharmaceutically acceptable carrier.

The present invention also relates to a method of treating or preventing a disorder in a mammal, including a human, resulting from an excess of substance P, comprising administering to said mammal a substance P antagonizing amount of a compound of the formula I, or a pharmaceutically acceptable salt thereof.

The present invention also relates to a pharmaceutical composition for treating or preventing a disorder in a mammal, including a human, the treatment or prevention of which is effected or facilitated by a decrease in substance P mediated neurotransmission, comprising an amount of a compound of the formula I, or a pharmaceutically acceptable salt thereof, effective in antagonizing the effect of substance P at its receptor site, and a pharmaceutically acceptable carrier.

The present invention also relates to a method of treating or preventing a disorder in mammal, including a human, the treatment or prevention of which is effected or facilitated by a decrease in substance P mediated neurotransmission, comprising administering to said mammal an amount of a compound of the formula I, or a pharmaceutically acceptable salt thereof, effective in antagonizing the effect of substance P at its receptor site.

The present invention also relates to a pharmaceutical composition for treating or preventing a disorder in a mammal, including a human, the treatment or prevention of which is effected or facilitated by a decrease in substance P mediated neurotransmission, comprising an amount of a compound of the formula I, or a pharmaceutically acceptable salt thereof, effective in treating or preventing such disorder, and a pharmaceutically acceptable carrier.

The present invention also relates to a method of treating or preventing a disorder in mammal, including a human, the treatment or prevention of which is effected or facilitated by a decrease in substance P mediated neurotransmission, comprising administering to said mammal an amount of a compound of the formula I, or a pharmaceutically acceptable salt thereof, effective in treating or preventing such disorder.

The compounds of the formula I have chiral centers and therefore exist in different enantiomeric forms. This invention relates to all optical isomers and all stereoisomers of compounds of the formula I, and mixtures thereof.

DETAILED DESCRIPTION OF THE INVENTION

The following reaction schemes illustrate the preparation of the compounds of the present invention. Unless otherwise indicated, A, G, $R^1$, $R^2$, $R^3$, $R^4$, $R^5$, $R^6$ and $R^7$ in the reaction schemes and discussion that follow are defined as above.

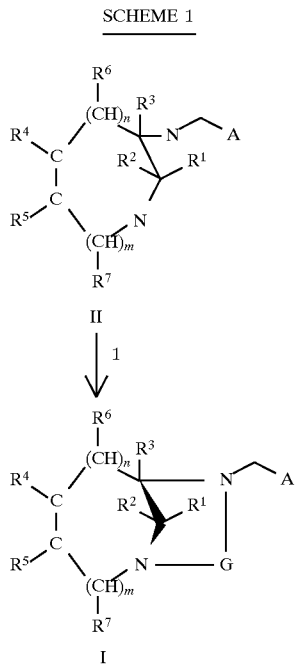

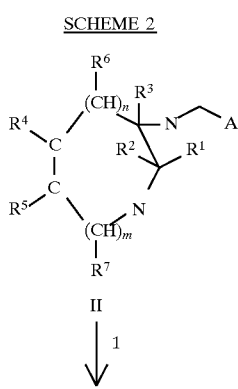

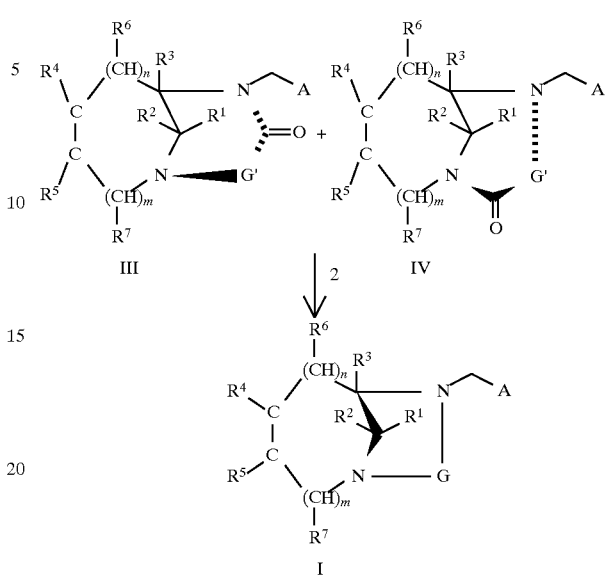

In Reaction 1 of Scheme 1, the amino heterocyclic compound of formula II is converted to the corresponding diazabicyclic compound of formula I by, first, heating II to reflux in the presence of a base. After being heated for a time period between about one hour to about three hours, preferably about two hours, the reaction mixture is (1) cooled to about 0° C. to about 45° C., preferably about room temperature, (2) treated dropwise with an alkylating agent of the formula $E^1$—G—$E^2$, wherein G is as defined above and $E^1$ and $E^2$ are independently selected from the group consisting of chloro, bromo, iodo, mesylate, tosylate and benzyloxy, and (3) allowed to stir for a time period between about 1 hour to about 24 hours, preferably overnight for convenience. Suitable solvents include tetrahydrofuran, diethyl ether, dioxane, dimethylacetamide and dimethylformamide, preferably tetrahydrofuran, and suitable bases include sodium hydride, sodium carbonate and potassium carbonate, preferably sodium hydride.

Alternatively, the compound of formula II may also be converted to the corresponding diazabicyclic compound of formula I by treating II with an aldehyde of the formula, $R^8$CHO, wherein $R^8$ is as defined above, in a polar protic solvent, preferably methanol, and heating the reaction mixture to reflux for a time period between about 1 hour to about 24 hours, preferably 12 hours.

In Reaction 1 of Scheme 2, the amino heterocyclic group of formula II is converted to the corresponding lactam compounds of formulae III and IV by reacting II with an acetyl compound of the formula $E^1$—G'—CO—$E^2$, wherein $E^1$ and $E^2$ are as defined above and G' is $(CR^8R^9)_p$ wherein $R^8$ and $R^9$ are as defined above and p is an integer from 1 to 3, in the presence of a base, preferably triethylamine. Suitable solvents include tetrahydrofuran, diethyl ether, dioxane, dimethylacetamide and dimethylformamide, preferably tetrahydrofuran. The reaction mixture is allowed to stir at a temperature of about 15° C. to about 40° C., preferably about 25° C., for a time period of about 1 hour to about 24 hours, preferably about 12 hours.

In Reaction 2 of Scheme 2, after a conventional workup of the intermediates formed in Reaction 1, the lactam compounds of formulae III and IV are converted to the corresponding diazabicyclic compound of formula I by reacting III and IV with reducing agent, such as borane tetrahydrofuran complex, lithium aluminum hydride or borane methyl sulfide complex, preferably borane tetrahydrofuran complex. Suitable solvents include tetrahydrofuran, diethyl ether, dioxane, dimethylacetamide and dimethylformamide, preferably tetrahydrofuran. The reaction mixture is heated to reflux and allowed to stir for a time period between about 30 minutes to about 90 minutes, preferably about 60 minutes.

The therapeutic compounds of the present invention exhibit substance P receptor-binding activity and therefore are of value in the treatment and prevention of a wide variety of clinical conditions, the treatment or prevention of which are effected or facilitated by a decrease in substance P mediated neurotransmission. Such conditions include inflammatory diseases (e.g., arthritis, psoriasis, asthma and inflammatory bowel disease), anxiety, depression or dysthymic disorders, urinary incontinence, gastrointestinal disorders such as emesis and colitis, psychosis, pain, sunburn, diseases caused by *Helicobacter pylori* or another urease-positive gram-negative bacterium, conditions that are caused or mediated by angiogenesis or of which angiogenesis is a symptom, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis. Hence, these compounds are readily adapted to therapeutic use as substance P antagonists for the control and/or treatment of any of the aforesaid clinical conditions in mammals, including humans.

The therapeutic compounds of the present invention can be administered via the oral, parenteral or topical routes. In general, these compounds are most desirably administered in dosages ranging from about 5.0 mg up to about 1500 mg per day, although variations will necessarily occur depending upon the weight and condition of the subject being treated and the particular route of administration chosen. However, a dosage level that is in the range of about 0.07 mg to about 21 mg per kg of body weight per day is most desirably employed. Variations may nevertheless occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

The compounds of the formula I and their pharmaceutically acceptable salts ("the therapeutic compounds") may be administered alone or in combination with pharmaceutically acceptable carriers or diluents by of the three routes previously indicated, and such administration may be carried out in single or multiple doses. More particularly, the therapeutic compounds of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutic compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a therapeutic compound of the present invention in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The activity of the therapeutic compounds of the present invention as substance P receptor antagonists may be determined by their ability to inhibit the binding of substance P at its receptor sites in bovine caudate tissue, employing radioactive ligands to visualize the tachykinin receptors by means of autoradiography. The substance P antagonizing activity of the herein described compounds may be evaluated by using the standard assay procedure described by M. A. Cascieri et al., as reported in the *Journal of Biological Chemistry*, Vol. 258, p. 5158 (1983). This method essentially involves determining the concentration of the individual compound required to reduce by 50% the amount of radiolabelled substance P ligands at their receptor sites in said isolated cow tissues, thereby affording characteristic $IC_{50}$ values for each compound tested.

In this procedure, bovine caudate tissue is removed from a −70° C. freezer and homogenized in 50 volumes (w./v.) of an ice-cold 50 mM Tris (i.e., trimethamine which is 2-amino-2-hydroxymethyl-1,3-propanediol) hydrochloride buffer having a pH of 7.7. The homogenate is centrifuged at 30,000×G for a period of 20 minutes. The pellet is resuspended in 50 volumes of Tris buffer, rehomogenized and then recentrifuged at 30,000×G for another twenty-minute period. The pellet is then resuspended in 40 volumes of ice-cold 50 mM Tris buffer (pH 7.7) containing 2 mM of calcium chloride, 2 mM of magnesium chloride, 4 µg/ml of bacitracin, 4 µg/ml of leupeptin, 2 µg of chymostatin and 200 g/ml of bovine serum albumin. This step completes the production of the tissue preparation.

The radioligand binding procedure is then carried out in the following manner, viz., by initiating the reaction via the addition of 100 µl of the test compound made up to a concentration of 1 µM, followed by the addition of 100 µl of radioactive ligand made up to a final concentration 0.5 mM and then finally by the addition of 800 µl of the tissue preparation produced as described above. The final volume is thus 1.0 ml, and the reaction mixture is next vortexed and incubated at room temperature (about 20° C.) for a period of 20 minutes. The tubes are then filtered using a cell harvester, and the glass fiber filters (Whatman GF/B) are washed four times with 50 mM of Tris buffer (pH 7.7), with the filters having previously been presoaked for a period of two hours prior to the filtering procedure. Radioactivity is then determined in a Beta counter at 53% counting efficiency, and the $IC_{50}$ values are calculated by using standard statistical methods.

The ability of the therapeutic compounds of this invention to inhibit substance P induced effects in vivo may be determined by the following procedures "a" through "d". (Procedures "a" through "c" are described in Nagahisa et al., *European Journal of Pharmacology*, 217, 191–5 (1992), which is incorporated herein by reference in its entirety.)

a. Plasma Extravasation in the Skin

Plasma extravasation is induced by intradermal administration of substance P (50 µl, 0.01% BSA-saline solution) in dorsal skin of pentobarbital (25 mg/kg i.p.) anesthetized male Hartley guinea pigs weighing 450–500 g. The compound to be tested is dissolved in 0.1% methyl cellulose-water (MC) and dosed p.o. 1 hour before substance P challenge (3 pmol/site). Evans blue dye (30 mg/kg) is administered intravenously 5 minutes before challenge. After 10 minutes, the animals are sacrificed, the dorsal skin is removed, and the blue spots are punched out using a cork borer (11.5 mm oral dose (o.d.)). Tissue dye content is quantitated after overnight formamide extraction at 600 nm absorbance.

b. Capsaicin-induced Plasma Extravasation

Plasma extravasation is induced by intraperitoneal injection of capsaicin (10 ml of 30 µM solution in 0.1% BSA/saline) into pentobarbital anesthetized (25 mg/kg i.p.) guinea pigs. The compound to be tested is dissolved in 0.1% MC and dosed p.o. 1 hour before capsaicin challenge. Evans blue dye (30 mg/kg) is administered i.v. 5 minutes before challenge. After 10 minutes, the animals are sacrificed, and both right and left ureters are removed. Tissue dye content is quantitated as in "a" above.

c. Acetic Acid-induced Abdominal Stretching

Male ddY mice (SLC, Japan), weighing 14–18 g, were fasted overnight. The compound to be tested is dissolved in 0.1% MC and dosed p.o. 0.5 hour before acetic acid (AA) injection (0.7%, 0.16 ml/10 g body weight). The animals are placed in clear beakers (1 per beaker) and the stretching response is counted 10 to 20 minutes after the AA injection (10 minute interval).

d. Substance P-induced Hyperlocomotor Paradigm

The anti-psychotic activity of the therapeutic compounds of the present invention as neuroleptic agents for the control of various psychotic disorders may be determined by a study of their ability to suppress substance P-induced or substance P agonist induced hypermotility in guinea pigs. This study is carried out by first dosing the guinea pigs with a control compound or with an appropriate test compound of the present invention, then injecting the guinea pigs with substance P or a substance P agonist by intracerebral administration via canula and thereafter measuring their individual locomotor response to said stimulus.

The anti-emetic activity of compounds that are substance P receptor antagonists may be determined by evaluating their ability to reduce the percentage of ferrets exhibiting emesis in response to cisplatinum exposure (10 mg/kg, i.p.). The compound (2S, 3S)-N-(5-isopropyl-2-methoxyphenyl) methyl-2-diphenylmethyl-1-azabicyclo[2.2.2]octan-3-amine inhibited cisplatinum induced emesis in ferrets when administered at a dose of 1 mg/kg s.c. (subcutaneously), 30 minutes before cisplatinum exposure. The compound (2S, 3S)-3-(2-methoxy-5-trifluoromethyoxybenzyl)-amino-2-phenylpiperidine inhibited cisplatinum induced emesis in ferrets when administered at a dose of 1 mg/kg s.c., 30 minutes before cisplatinum exposure. The compound cis-3-[(2-methoxyphenyl)methylamino]-2-benzhydrylquinuclidine inhibited cisplatinum induced emesis in ferrets when administered at a dose of 10 mg/kg s.c., 30 minutes before cisplatinum exposure.

The anti-sunburn activity of compounds that are substance P receptor antagonists may be determined by evaluating the compounds according to the following ultraviolet (UV) Erythema Model.

Male Hartley guinea pigs (5 weeks old) may be used for these experiments. The dorsal hair of the animals is removed 2 days before treatment with an electric shaver and hair remover cream (EBA cream Tokyo Tanabe Pharmaceuticals). The animals are then fasted over night.

The dorsal skin of the guinea pigs is then exposed to UV light (1650–1670 Lux, 60 sec) to induce a sunburn-like inflammation.

Erythema may be determined by visual scoring (0: none, 1: slightly and 2: clear) or by plasma extravasation. Plasma extravasation may be determined by Evans blue dye method (Guinea pigs are anesthetized with 25 mg/kg i.p. of pentobarbitol and 10 minutes later, the dye 30 mg/kg is injected intravenous). The scoring and plasma extravasation may be determined at 2, 5, 18 and 24 hours after the UV-irradiation.

The present invention is illustrated by the following examples. It will be understood, however, that the invention is not limited to the specific details of these examples.

EXAMPLE 1

6-(2-Methoxybenzyl)-8-phenyl-1,6-diazabicyclo[3.2.1]octane

Sodium hydride (1.47 g, 36.8 mmol of a 60% dispersion in oil) was added to a round-bottomed flask fitted with an $N_2$ inlet, condensor, stirrer and washed with hexane to remove the oil. Anhydrous tetrahydrofuran (THF), 50 mL, was added followed by 6.30 grams (18.9 mmol) of (2S, 3S)-3-(2-methoxybenzylamino)-2-phenylpiperidine in 50 mL of tetrahydrofuran. After heating to reflux for two hours, the mixture was allowed to cool to room temperature and was treated dropwise with benzyl chloromethyl ether (5.1 mL, 36.8 mmol). The mixture was stirred overnight and the excess sodium hydride quenched with water. After being stirred an additional hour, the organic layer was separated and the aqueous layer was extracted with methylene chloride. The organic layers were combined and washed with saturated aqueous sodium chloride before drying over magnesium sulfate. Concentration in vacuo gave a solid which recrystallized from methanol/methylene chloride to a white solid, 2.36 grams (40%), mp 105°–107° C. Mass Spectrum (m/e): 309 ($M^{+1}$, 100%), 159 (12%). $^1$H-NMR ($CDCl_3$) δ1.45–2.20 (m, 5H), 3.15 (m, 2H), 3.5 (d, 1H), 3.65–3.85 (m, 2H), 3.75 (s, 3H), 3.95 (d, 1H), 4.10 (d, 1H), 6.8 (d, 1H), 6.95 (t, 1H), 7.15–7.6 (m, 7H). Anal. Calc'd for $C_{20}H_{24}N_2O$: C, 77.88; H, 7.83, N, 9.08. Found: C, 77.72; H, 7.75; N, 9.04.

EXAMPLE 2

4-(2-Methoxybenzyl)-9-phenyl-1,4-diazabicyclo [3.3.1]nonane

A. To a solution of (2S, 3S)-3-(2-methoxybenzylamino)-2-phenylpiperidine (1.50 grams, 4.06 mmol) and triethylamine (0.66 ml, 4.05 mmol) in tetrahydrofuran (10 mL) was added chloroacetyl chloride (0.32 ml, 4.06 mmol) dropwise. The solution was allowed to stir at 25° C. for 12 hours. The reaction was quenched by pouring into water and stirring for 1 hour. The biphasic mixture was extracted with ethyl acetate. The combined organic extracts were dried over magnesium sulfate and evaporated in vacuo to yield a yellow oil. The oil was chromatographed on silica gel using a 1:5:94 ratio of ammonium hydroxide/methanol/methylene chloride as the eluent, to yield a light yellow oil (480 mg, 32%). $^1$H NMR (250 MHz, $CDCl_3$): δ7.7–7.6 (m, 2H), 7.5–7.2 (m, 5H), 7.0–6.8 (m, 2H), 6.1 (d, 1H), 4.5–3.0 (m, 11H), 2.1–1.7 (m, 5H). Mass spectrum (m/e): 373 ($m^+$).

B. To a solution of the above intermediate (480 mg. 1.29 mmol) in tetrahydrofuran (10 mL), potassium t-butoxide (180 mg. 1.40 mmol) was added slowly over 10 minutes. After stirring the reaction mixture was stirred at 25° C. for 12 hours, the reaction was quenched by the slow addition of water and allowed to stir for 30 minutes, the layers were separated and the aqueous layer was extracted with ethyl acetate. The combined organic layers were dried over magnesium sulfate, treated with activated carbon, filtered through diatomaceous earth (d.e.), and evaporated in vacuo to an oil. The oil was converted to the hydrochloride salt in methylene chloride/diethyl ether by bubbling hydrochloric gas through the solution for 10 minutes. The solvent was evaporated in vacuo and the residue recrystallized from methanol/ether, to yield a yellow amorphous solid (88 mg, 18%). $^1$H NMR (250 MHz, $CDCl_3$, free base) δ7.6 (m, 1H), 7.4–7.2 (m, H), 6.9–6.8 (m, 2H), 4.4–4.39 (m, 1H), 2.2–3.5 (m, 7H), 3.2–3.1 (m, 2H), 2.1–1.2 (m, 7H). Mass spectrum (m/e): 336 ($m^+$), 215.

C. The preceding hydrochloride salt (88 mg, 0.23 mmol) was converted to the free base by dissolving it in saturated aqueous sodium bicarbonate and extracting with methylene chloride. The organic layers were dried over magnesium sulfate and evaporated in vacuo to yield a yellow oil. This oil was then dissolved in tetrahydrofuran (3 mL) and borane tetrahydrofuran complex (0.26 ml, 1N in THF) was added dropwise. The solution was heated to reflux and allowed to stir for 1 hour. The reaction mixture was allowed to cool to room temperature and was quenched by the slow addition of water. The solution was stirred for 30 minutes and evaporated in vacuo. The residue was then dissolved in water and extracted with methylene chloride, which was dried over magnesium sulfate and evaporated to an oil. The oil was chromatographed on silica gel using a 1:5:94 ratio of ammonium hydroxide/methanol/methylene chloride as the eluent to produce a light yellow oil. The oil was converted to the hydrochloride salt by dissolving it in methylene chloride/diethyl ether and adding 4N hydrochloric acid in dioxane (0.50 mL). The solution was allowed to stir for 30 minutes, evaporated in vacuo and the residue was recrystallized from methanol/diethyl ether, to produce a light yellow amorphous solid, 21 mg. $^1$H NMR (250 MHz, $CDCl_3$): δ7.7 (d, 2H), 7.4–7.0 (m, 6H), 6.9 (d, 2H), 4.0–3.8 (m, 5H), 3.7 (d, 1H), 3.5 (m, $_1$H), 3.3 (m, 1H), 3.2 (bs, 1H), 3.2–2.9 (m, 2H), 2.7–2.6 (m, 2H), 2.5 (m, 1H), 2.2–1.8 (m, 2H), 1.7–1.5 (m, 1H). High resolution mass spectrum (HRMS): calc'd: 322.2039; found 322.2068.

We claim:

1. A compound of the formula

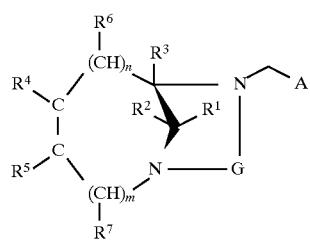

or a pharmaceutically acceptable salt thereof wherein $R^1$ is phenyl, thienyl or benzhydryl wherein one of the phenyl moieties of said benzhydryl may optionally be replaced by naphthyl, thienyl, furyl or pyridyl and wherein said phenyl, thienyl and benzhydryl may be substituted with one or more substituents independently selected from halo, nitro, $(C_1-C_6)$alkyl optionally substituted with from one to three fluorine atoms, $(C_1-C_6)$alkoxy optionally substituted with from one to three fluorine atoms, amino, hydroxy$(C_1-C_6)$alkyl, $(C_1-C_6)$alkoxy$(C_1-C_6)$alkyl, $(C_1-C_6)$-alkylamino, $(C_1-C_6)$alkyl—O—CO—, $(C_1-C_6)$alkyl—CO—O—, $(C_1-C_6)$alkyl—CO—, $(C_1-C_6)$alkyl—O—, $(C_1-C_6)$alkyl—CO—$(C_1-C_6)$alkyl-, di-$(C_1-C_6)$alkylamino, —CONH—$(C_1-C_6)$alkyl, $(C_1-C_6)$-alkyl—CO—NH—$(C_1-C_6)$alkyl, —NHCOH and —NHCO—$(C_1-C_6)$alkyl;

$R^2$ is hydrogen or $(C_1-C_6)$alkyl, or $R^1$ and $R^2$, together with the carbon to which they are attached, form a saturated carbocyclic ring having from 3 to 7 carbon atoms;

A is phenyl, thienyl, benzothiazolyl or naphthyl wherein said phenyl, thienyl, benzothiazolyl and naphthyl may be substituted with one or more substituents independently selected from halo, nitro, $(C_1-C_6)$alkyl optionally substituted with from one to three fluorine atoms, $(C_1-C_6)$alkoxy optionally substituted with from one to three fluorine atoms, amino, hydroxy$(C_1-C_6)$alkyl, $(C_1-C_6)$alkoxy$(C_1-C_6)$alkyl, $(C_1-C_6)$-alkylamino, $(C_1-C_6)$alkyl—O—CO—, $(C_1-C_6)$alkyl—CO—O—, $(C_1-C_6)$alkyl—CO—, $(C_1-C_6)$alkyl—O—, $(C_1-C_6)$alkyl—CO—$(C_1-C_6)$alkyl-, di-$(C_1-C_6)$alkylamino, —CONH—$(C_1-C_6)$alkyl, $(C_1-C_6)$-alkyl—CO—NH—$(C_1-C_6)$alkyl, —NHCOH and —NHCO—$(C_1-C_6)$alkyl;

n is 0, or 1;

m is 0, or 1;

the sum of n and m is 1;

$R^3$ is hydrogen or $(C_1-C_6)$alkyl optionally substituted with one to three fluorine atoms;

$R^4$ and $R^5$ are hydrogen, or $R^4$ and $R^5$, together with the carbons to which they are attached, form an aromatic or non-aromatic carbocyclic or heterocyclic ring;

$R^6$ and $R^7$ are hydrogen, or $R^3$ together with $R^4$, $R^5$, $R^6$ or $R^7$, along with the carbon to which they are attached, form a saturated carbocyclic group having from 3 to 6 carbons;

G is $(CR^8R^9)_p$ wherein p is 1, and $R^8$ and $R^9$ are each independently selected from hydrogen, $(C_1-C_6)$alkyl, phenyl, naphthyl or heteroaryl wherein said alkyl may be substituted by one to three fluorine atoms.

2. A compound according to claim 1, wherein $R^1$ is phenyl or benzhydryl.

3. A compound according to claim 1, wherein A is 2-methoxyphenyl, 2-trifluoromethoxyphenyl or 5-methoxybenzothiazole.

4. A compound according to claim 1, wherein n is 1, m is 0, p is 1, $R^1$ is phenyl and A is benzothiazolyl.

5. A compound according to claim 1, wherein n is 1, m is 0, p is 1, $R^1$ is phenyl and A is methoxyphenyl, trifluoromethoxyphenyl or methoxy(trifluoromethoxy)phenyl.

6. A compound according to claim 1, wherein $R^1$ is phenyl, thienyl or benzhydryl which may be substituted with one to three substituents.

7. A compound according to claim 1, wherein A is phenyl, thienyl, benzothiazolyl or naphthyl which may be substituted with one to three substituents.

8. A compound according to claim 1, wherein said aromatic or non-aromatic heterocyclic ring is piperidine, indoline, pyridine, thiophene and pyrimidine.

9. A compound according to claim 1, said compound being selected from the group consisting of:

6-(2-methoxybenzyl)-8-phenyl-1,6-diazabicyclo[3.2.1]octane;

8-phenyl-6-(2-trifluoromethoxybenzyl)-1,6-diazabicyclo[3.2.1]octane;

6-(2-methoxybenzyl)-7-methyl-8-phenyl-1,6-diazabicyclo[3.2.1]octane;

6-(2-methoxybenzyl)-7,7-dimethyl-8-phenyl-1,6-diazabicyclo[3.2.1]octane;

5-methoxy-6-(8-phenyl-1,6-diazabicyclo[3.2.1]oct-6-ylmethyl)benzothiazole;

5-methoxy-2-methyl-6-(8-phenyl-1,6-diazabicyclo[3.2.1]oct-6-ylmethyl)benzothiazole;

5-methoxy-2-phenyl-6-(8-phenyl-1,6-diazabicyclo[3.2.1]oct-6-ylmethyl)benzothiazole;

5-methoxy-2-trifluoromethyl-6-(8-phenyl-1,6-diazabiyclo[3.2.1]oct-6-ylmethyl)-benzothiazole;

6-(2-methoxy-5-trifluoromethoxybenzyl)-8-phenyl-1,6-diazabicyclo[3.2.1]octane.

10. A pharmaceutical composition for treating or preventing a condition selected from the group consisting of inflammatory diseases, anxiety, colitis, depression or dysthymic disorders, urinary incontinence, gastrointestinal disorders such as emesis, psychosis, pain, sunburn, diseases caused by *Helicobacter pylori* or another urease-positive gram-negative bacterium, conditions that are caused or mediated by angiogenesis or of which angiogenesis is a symptom, allergies, chronic obstructive airways disease, hypersensitivity disorders, vasospastic diseases, fibrosing and collagen diseases, reflex sympathetic dystrophy, addiction disorders, stress related somatic disorders, peripheral neuropathy, neuralgia, neuropathological disorders, disorders related to immune enhancement or suppression and rheumatic diseases in a mammal, comprising an amount of a compound according to claim 1 effective in preventing or treating such condition and a pharmaceutically acceptable carrier.

11. A method of treating or preventing a condition selected from the group consisting of inflammatory diseases anxiety, colitis, depression or dysthymic disorders, urinary incontinence, emesis, psychosis, pain, sunburn, diseases caused by *Helicobacter pylori* or another urease-positive gram-negative bacterium, conditions that are caused or mediated by angiogenesis or of which angiogenesis is a symptom, allergies, chronic obstructive airways disease, hypersensitivity disorders, vasospastic diseases, fibrosing and collagen diseases, reflex sympathetic dystrophy, addiction disorders, stress related somatic disorders, peripheral neuropathy, neuralgia, neuropathological disorders, disorders related to immune enhancement or suppression and rheumatic diseases in a mammal, comprising administering to a mammal in need of such treatment or prevention an amount of a compound according to claim 1 effective in preventing or treating such condition.

12. A pharmaceutical composition for antagonizing the effects of substance P in a mammal, comprising a substance P antagonizing effective amount of a compound according to claim 1 and a pharmaceutically acceptable carrier.

13. A method of antagonizing the effects of substance P in a mammal, comprising administering to said mammal a substance P antagonizing effective amount of a compound according to claim 1.

14. A pharmaceutical composition for treating or preventing a condition in a mammal, the treatment or prevention of which is effected or facilitated by a decrease in substance P mediated neurotransmission, comprising an amount of a compound according to claim 1 effective in antagonizing the effect of substance P at its receptor site and a pharmaceutically acceptable carrier.

15. A method of treating or preventing a condition in a mammal, the treatment or prevention of which is effected or facilitated by a decrease in substance P mediated neurotransmission, comprising administering to a mammal in need of such treatment or prevention an amount of a compound according to claim 1, or a pharmaceutically acceptable salt thereof, effective in antagonizing the effect of substance P at its receptor site.

16. A pharmaceutical composition for treating or preventing a condition in a mammal, the treatment or prevention of which is effected or facilitated by a decrease in substance P mediated neurotransmission, comprising an amount of a compound according to claim 1, or a pharmaceutically acceptable salt thereof, effective in treating or preventing such condition and a pharmaceutically acceptable carrier.

17. A method of treating or preventing a condition In a mammal, the treatment or prevention of which is effected or facilitated by a decrease in substance P mediated neurotransmission, comprising administering to a mammal in need of such treatment or prevention an amount of a compound according to claim 1 effective in treating or preventing such condition.

* * * * *